United States Patent
Solarski et al.

(10) Patent No.: US 11,083,712 B1
(45) Date of Patent: Aug. 10, 2021

(54) LOW CONCENTRATION DELIVERY OF AN ERGOLINE DERIVATIVE FOR TREATMENT OF A HEADACHE

(71) Applicant: Relevale, Inc., Alpharetta, GA (US)

(72) Inventors: Ralph Solarski, Alpharetta, GA (US); Robert Edward Malone, Northborough, MA (US)

(73) Assignee: RELEVALE, INC., Alpharetta, GA (US)

(*) Notice: Subject to any disclaimer, the term of this patent is extended or adjusted under 35 U.S.C. 154(b) by 102 days.

(21) Appl. No.: 16/359,313

(22) Filed: Mar. 20, 2019

Related U.S. Application Data

(60) Provisional application No. 62/645,212, filed on Mar. 20, 2018.

(51) Int. Cl.
| | |
|---|---|
| *A61M 5/20* | (2006.01) |
| *A61K 31/437* | (2006.01) |
| *A61P 25/06* | (2006.01) |
| *A61M 5/28* | (2006.01) |
| *A61M 5/32* | (2006.01) |
| *A61M 5/31* | (2006.01) |

(52) U.S. Cl.
CPC ......... *A61K 31/437* (2013.01); *A61M 5/2033* (2013.01); *A61M 5/281* (2013.01); *A61M 5/3202* (2013.01); *A61P 25/06* (2018.01); *A61M 2005/206* (2013.01); *A61M 2005/3139* (2013.01)

(58) Field of Classification Search
CPC .... A61M 5/2033; A61M 5/20; A61M 5/3204; A61M 5/30; A61M 5/2448; A61M 5/24; A61M 5/19; A61M 5/3157; A61K 9/0019; A61K 45/06
See application file for complete search history.

(56) References Cited

U.S. PATENT DOCUMENTS

| | | | |
|---|---|---|---|
| 8,945,067 B2* | 2/2015 | McLoughlin | A61M 5/3213 604/192 |
| 2003/0106824 A1* | 6/2003 | Wilmot | A61M 5/2033 206/439 |
| 2008/0287451 A1* | 11/2008 | Cook | A61K 31/48 514/250 |
| 2014/0179705 A1* | 6/2014 | Armer | C07D 498/04 514/250 |
| 2016/0235664 A1* | 8/2016 | Wotton | A61M 5/20 |
| 2019/0000753 A1* | 1/2019 | Narasimha Murthy | A61K 47/32 |

OTHER PUBLICATIONS

Lippincott's Nursing Procedures, Fifth Edition. (Year: 2004).*

* cited by examiner

*Primary Examiner* — Manuel A Mendez
(74) *Attorney, Agent, or Firm* — Patrick B. Horne; Shumaker, Loop & Kendrick, LLP

(57) ABSTRACT

Provided are ergoline derivative containing medicaments disposed within a preassembled, prefilled, single-use delivery device, methods for administering a medicament using a preassembled, prefilled, single-use delivery device, and systems or kits that contain one or more preassembled, prefilled, single-use devices and user instructions, such as for treatment of a migraine or other headache.

36 Claims, 7 Drawing Sheets

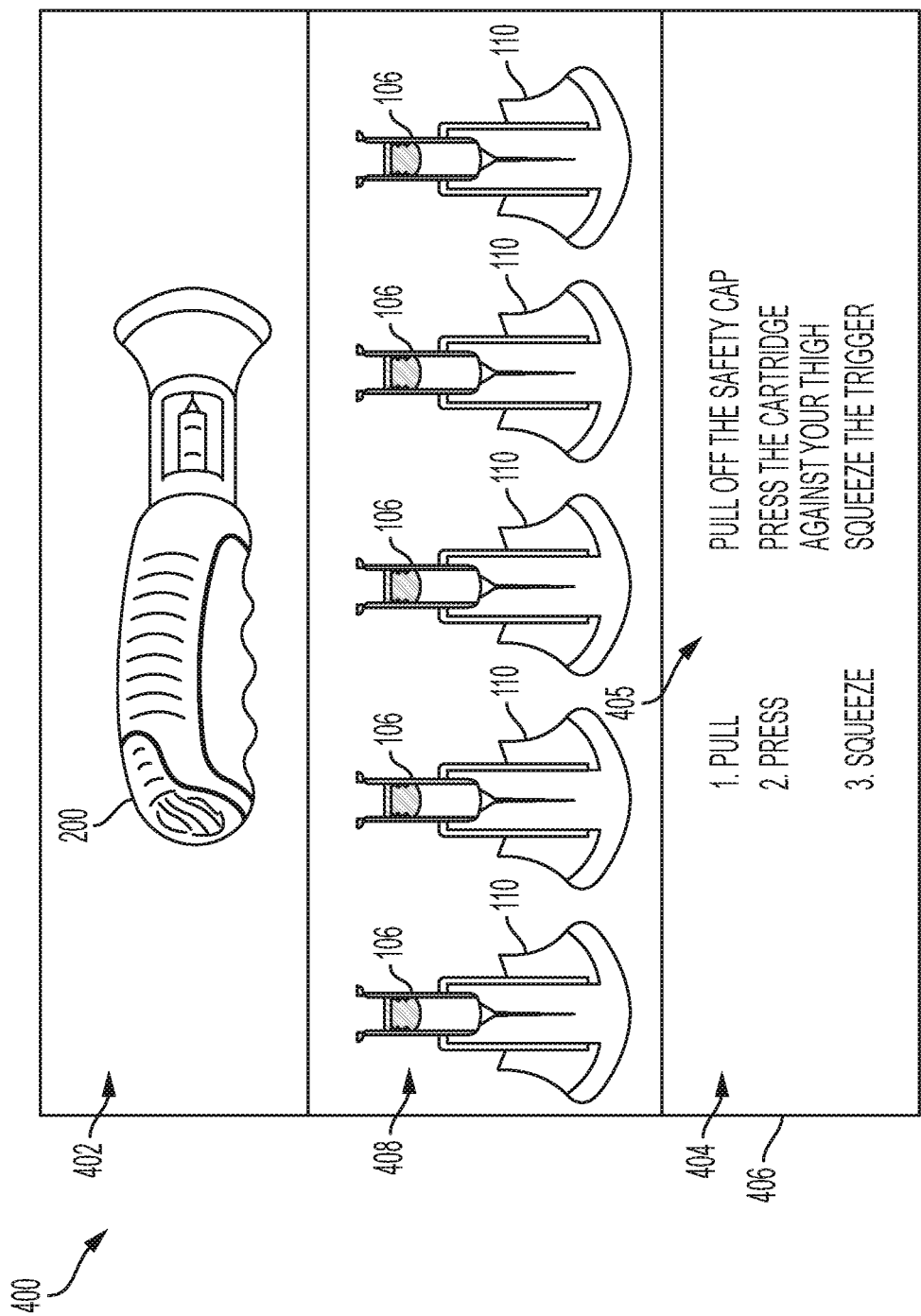

LOW CONCENTRATION DELIVERY OF AN ERGOLINE DERIVATIVE FOR TREATMENT OF A HEADACHE

CROSS-REFERENCE TO RELATED APPLICATIONS

This application claims priority under 35 U.S.C. § 119(e) to U.S. Provisional Application No. 62/645,212 filed Mar. 20, 2018, entitled "Low Concentration Delivery of an Ergoline Derivative For Treatment of a Headache," the disclosure of which is herein incorporated by reference in its entirety.

BACKGROUND OF THE INVENTION

Migraine is a genetic neurological disease characterized by episodes of migraine attacks. According to the National Headache Foundation, more than 37 million people in the United States suffer from migraines the majority of sufferers experience migraine attacks once or twice per month and more than 4 million people are experiencing at least 15 migraine days per month. The Migraine Research Foundation reports that migraine is the sixth most disabling illness in the world resulting in 1.2 million emergency room visits a year. This disease takes a significant toll on society. The Migraine Research Foundation reports more than Ninety percent of sufferers miss work or cannot function normally during a migraine attack and 20% of chronic migraine sufferers are classified as disabled. From an economic perspective, the Migraine Research Foundation reports that migraines are responsible for thirty-six billion dollars of healthcare and lost productivity costs annually in the United States alone. For sufferers who obtain prescription medication, the most common abortive treatment are triptans. Advantageously, triptans may be orally administered and do not require parenteral administration to be effective. However, while triptans are effective for many migraine sufferers, a significant minority do not have an effective response to triptans. Additionally, a study with sumatriptan (currently the top selling triptan) showed that 45% of the sumatriptan-treated patients had headache reoccurrence within 24 hours after treatment. Winner, P, et al., "A Double-Blind Study of Subcutaneous Dihydroergotamine vs. Subcutaneous Sumatriptan in the Treatment of Acute Migraine." *Arc. Neurol.* 1996:53(2):180-4.

Cluster headaches are another neurological disease characterized by recurrent, excruciating unilateral headaches, typically around the eye. They are nicknamed "suicide headaches" because of the severity of pain and affect about 0.1 of the general population. Fischera, M, et al., "The Incidence and Prevalence of Cluster Headache: A Meta-Analysis of Population-Based Studies" *Cephalalgia* 28(6): 614-8. Attacks often occur in cluster cycles with no remissions over a year. Weaver-Agostoni, J. (2013) "Cluster Headache" *American Family Physician* 88(2):122-8. Treatments for acute attacks include oxygen and fast-acting triptans. Like migraines, a significant minority of cluster headache sufferers do not respond effectively to triptans.

Dihydroergotamine (DHE) is an ergot alkaloid and a derivative of ergotamine. Dihydroergotamine Mesylate is an ergotamine hydrogenated in the 9, 10 position as the mesylate salt. Dihydroergotamine Mesylate is a pharmaceutically acceptable salt of dihydroergotamine known chemically as ergotaman-3',6',18-trione,9,10-dihydro-12'-hydroxy-2'-methyl-5'-(phenylmethyl)-,(5'α)-,monomethanesulfonate and is represented by the following structural formula:

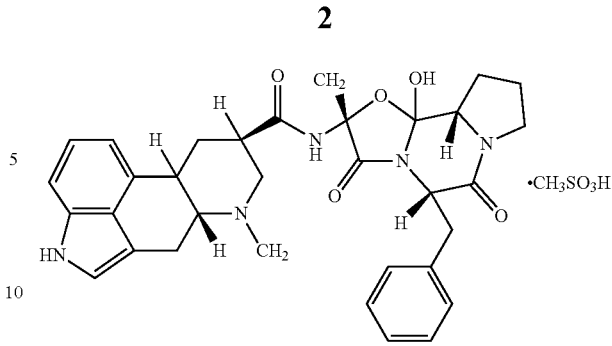

DHE has similar actions to triptans, acting as an agonist to the serotonin receptors and causing vasoconstriction of the intracranial blood vessels, but also interacts centrally with dopamine and adrenergic receptors. It binds with high affinity to 5-HT1Dα and 5-HT1Dβ receptors. It also binds with high affinity to serotonin 5-HT1A, 5-HT2A, and 5-HT2C receptors, noradrenaline α2A, α2B, and α, receptors, and dopamine D2L and D3 receptors.

Due to DHE's structure, it is poorly absorbed through the gut, and therefore oral dosage forms are not effective. Nasal DHE can be an effective dosage form but has been shown to have inconsistent effects. The nasal spray dosage form relies on uptake through tissues in the nose, which can lead to variable blood levels, with about 40% or less of the medication getting into the blood stream. Additionally, nearly half of the patients using the nasal spray dosage form complain of a bad taste after use. Matthew P., et al., "DHE: An Old Dog with New Tricks . . . Maybe?" *American Headache Foundation*, Aug. 18, 2015.

Parenteral DHE offers benefits including rapid uptake and more consistent absorption than the nasal form. A comparison study of subcutaneous sumatriptan and subcutaneous DHE in the treatment of acute migraine concluded that the reoccurrence of migraines was 2½ times more likely with sumatriptan than with DHE during a 24-hour follow-up period. Winner, P, et al., "A double-blind study of subcutaneous dihydroergotamine v. subcutaneous sumatriptan in the Treatment of Acute Migraine" *Arch. Neurol.* 1996; 53(2): 180-84.

Currently, a parenteral administration of DHE, either intravenous, intramuscular, or subcutaneous is provided in emergency rooms or under other clinical setting and requires direct contact with a health-care professional. Therefore, a person experiencing a migraine or other type of headache in need of treatment is required to travel to an emergency room or clinic where a medical professional may administer a high concentration dose of an ergoline derivative or other medication. As a result, the patient is required to suffer in severe pain and endure the other symptoms during the time spent traveling and the time waiting at the medical facility for treatment, which, depending on the distance to be traveled and the particular medical facility, could be in excess of several hours before the patient receives treatment. Further, intravenous injections of ergoline derivatives, such as DHE, commonly cause side effects such as nausea, vomiting, and increased blood pressure, particularly when administered at higher concentrations. The patient may suffer severe pain and other symptoms during the time spent traveling and awaiting treatment, only to have the relief provided by the treatment offset by the side effects of the high concentration of the ergoline derivative.

While the possibility may exist for a patient to self-inject DHE, the patient will require training on the preparation and administration of the DHE. For example, the prescribing information for D.H.E. 45® instructs that a patient requires professions instruction on how to properly administer the medication. The prescribing information continues to list 6 steps with a total of nineteen sub-steps to comply with while preparing for and administering a self-injection. These steps include, carefully examining the ampul of D.H.E. 45® for any cracks or breaks and the liquid for discoloration, cloudiness, or particles. Further, steps include how to draw the medication into the syringe by:

A. Wash your hands thoroughly with soap and water.
B. Check the dose of your medication.
C. Look to see if there is any liquid at the top of the ampul. If there is, gently flick the ampul with your finger to get all the liquid into the bottom portion of the ampul.
D. Hold the bottom of the ampul in one hand. Clean the ampul neck with an alcohol wipe using the other hand. To break, place the alcohol wipe around the neck of the ampul and break it open by pressing your thumb against the neck of the ampul.
E. Tilt the ampul down at a 45° angle. Insert the needle into the solution in the ampul. F. Draw up the medication by pulling back the plunger slowly and steadily until you reach your dose.
G. Check the syringe for air bubbles. Hold it with the needle pointing upward. If there are air bubbles, tap your finger against the barrel of the syringe to get the bubbles to the top. Slowly and carefully push the plunger up so that the bubbles are pushed out through the needle and you see a drop of medication.
H. When there are no air bubbles, check the dose of the medication. If the dose is incorrect, repeat steps F, G and H until you draw up the right dose. Each of these steps would be performed by a patient while suffering severe pain from a migraine and other side effect symptoms such as nausea, sensitivity to light, and sensitivity to sound, which creates added difficulty in completing those required steps.

Accordingly, a very real need currently exists for an improved medicament that contains a therapeutically effective amount of an ergoline derivative that can easily and quickly be administered outside of the clinical setting, thereby making it more viable for users to self-administer such a medicament when experiencing a migraine or other type of headache. Such a product would allow patients to receive treatment sooner, making treatment portable, and generally improving the user experience and accessibility to treatment.

Additionally, migraines and other headaches are a significant reason for emergency room visits, with over one-million visits per year in the U.S. alone. Accordingly, there exists a need to reduce demand on emergency rooms from patients experiencing a migraine or other headache. The present invention provides improvements which permit the treatment of migraines outside of a clinical setting in a manner that will quickly deliver the medicament to the user and effectively providing faster relief.

SUMMARY OF THE INVENTION

The inventive embodiments provided in this Summary of the Invention are meant to be illustrative only and to provide an overview of selective embodiments disclosed herein. The Summary of the Invention, being illustrative and selective does not limit the scope of any claim, does not provide the entire scope of the inventive embodiments disclosed or contemplated herein, and should not be construed as limiting or constraining the scope of this disclosure or any claimed inventive embodiment.

Presented herein are ergoline derivative containing medicaments disposed within a preassembled, prefilled, single-use delivery device.

In one aspect, the present invention relates to an ergoline derivative medicament comprising an ergot alkaloid, preferably dihydroergotamine (DHE) or a pharmaceutically acceptable salt such as dihydroergotamine mesylate, wherein the medicament is disposed in a preassembled, prefilled, single-use delivery device, such as an autoinjector, comprising a syringe containing the medicament, a hollow injection needle operably coupled to a distal end of the syringe; a dosing mechanism operably adjacent to a proximal end of the syringe; and a trigger mechanism that when actuated, causes the dosing mechanism to advance the syringe and the injection, and to discharge the medicament through the injection needle.

Methods of treating DHE-responsive migraine headaches, with or without aura, and cluster headache episodes by administering an ergoline derivative containing medicament comprising DHE with a preassembled, prefilled, single use delivery device while outside the clinical environment also are contemplated. In an exemplary method, a person suffering from a migraine headache would place an auto-injector device with a prefilled syringe against an injection site, actuate a trigger mechanism of the auto-injector device, and maintain the auto-injector device against the injection site, while an injection needle penetrates the injection site, and the medicament contained in the prefilled syringe is injected though the injection needle into the injection site. Methods of treating of treating DHE-responsive migraine and cluster headache episodes in a user that is not responsive to triptans is also contemplated.

In another aspect, the present disclosure embraces systems or kits for administering a medicament that contains an ergoline derivative. An exemplary system or kit may include one or more preassembled, prefilled, single-use delivery devices configured according to the present disclosure, and user instructions and/or mnemonic devices describing a method for administering the medicament.

BRIEF DESCRIPTION OF THE FIGURES

A full and enabling disclosure of the present invention, including the best mode thereof, directed to one of ordinary skill in the art, is set forth in the specification, which makes reference to the appended figures, in which:

FIGS. 4A-4C show exemplary systems or kits for administering a medicament that contains an ergoline derivative according to the present disclosure.

DETAILED DESCRIPTION OF REPRESENTATIVE EMBODIMENTS

Figure 1:
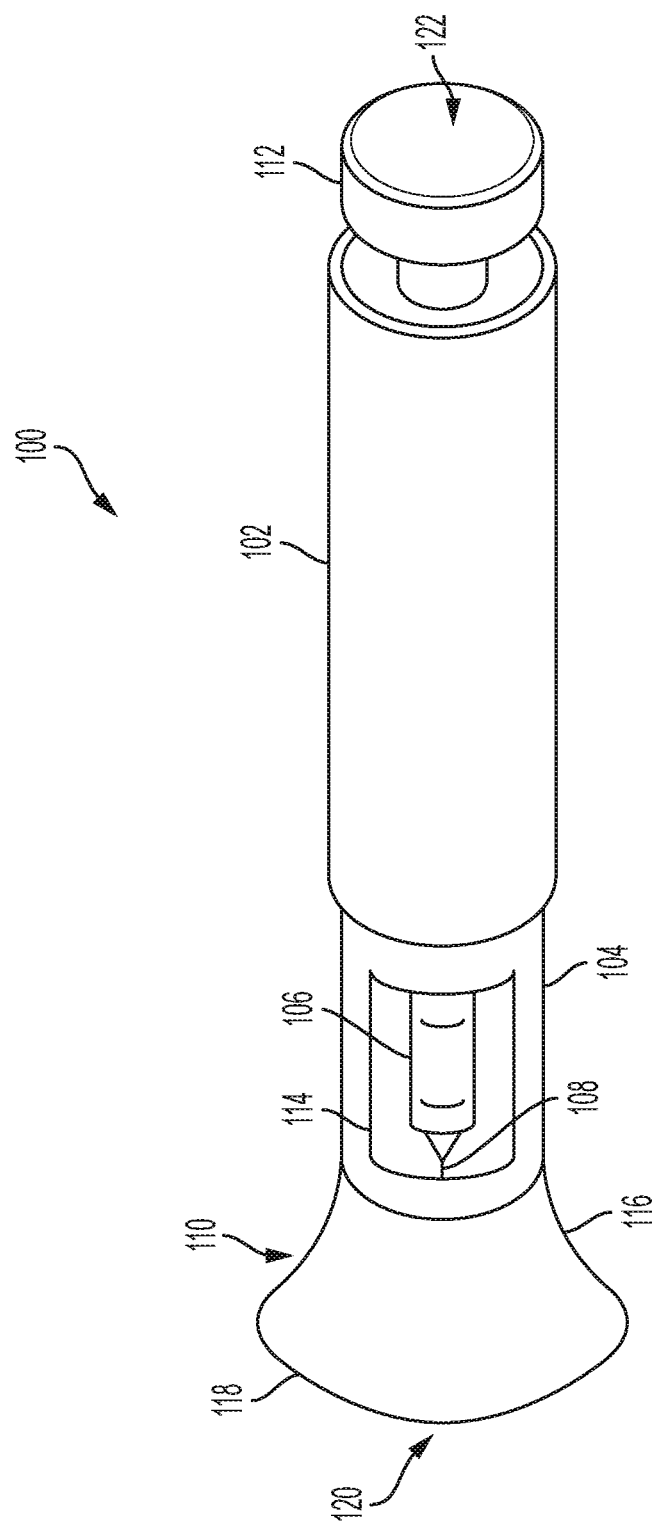
FIG. 1 is a perspective view of an exemplary delivery device according to the present disclosure.

Reference will now be made in detail to one or more embodiments of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

An ergoline derivative containing medicament is contemplated that contains an effective amount dihydroergotamine or a pharmaceutically acceptable salt thereof wherein the medicament is disposed in a preassembled, prefilled single-use delivery device comprising a syringe containing the medicament, a hollow injection needle operably coupled to a distal end of the syringe; a dosing mechanism operably adjacent to a proximal end of the syringe; and a trigger mechanism that when actuated, causes the dosing mechanism to advance the syringe and the injection, and to discharge the medicament through the injection needle.

A contemplated medicament comprises ergoline derivative, alcohol, glycerin, water for injection and optionally either sodium hydroxide or methane sulfonic acid. Preferably the ergoline derivative would be at a relatively low concentration such as 1.5 milligrams of ergoline derivative per milliliter of the medicament (mg/ml), in some embodiments from about 0.5 to about 1.4 mg/mL, and in some embodiments, from about 0.8 to about 1.2 mg/mL (e.g., 1 mg/mL). Without intending to be bound by theory, it is believed that the use of such a low concentration of the ergoline derivative can help to avoid or reduce side effects often associated with such compounds, such as nausea, vomiting, and increased blood pressure. Nevertheless, by selectively controlling the particular nature of the delivery mechanism, the ergoline derivative can still be administered in such a manner that it is effective for treating a patient with a headache. For example, the medicament is administered through an auto-injector that contains a syringe that is prefilled with the medicament having the desired low concentration of the ergoline derivative.

The syringe may contain the medicament in an amount sufficient so that from about 0.5 to about 3 milliliters (mL), in some embodiments from about 0.6 to about 2.8 mL, and in some embodiments, from about 0.7 to about 2.5 mL of the medicament are delivered per injection. In this regard, the ergoline derivative, such as for example dihydroergotamine mesylate, may, consequently, be delivered at a dosage level of from about 0.1 to about 10.0 milligrams (mg), in some embodiments from about 0.5 to about 3 mg, and in some embodiments, from about 1 to about 2 mg per injection. In an embodiment, the medicament is present as 1 ml of solution in a pre-filled autoinjector and includes 1 mg of dihydroergotamine mesylate. The dose can be self-administered by a patient, subcutaneously, preferably in the thigh. The administration can be repeated, as needed, at 1 hour intervals to a total dose of 3 mL, using multiple pre-filled autoinjector devices. Not only can such a delivery device administer an effective dosage of the ergoline derivative, but it can also provide a relatively simple and easy method for a patient to self-administer the medicament without the need for administration by a medical professional.

The presently disclosed delivery devices, systems or kits, and methods of administering a medicament that contains an ergoline derivative make it easier for users to administer such a medicament when experiencing a migraine or other type of headache, which can occur at any time without advance warning. The present disclosure additionally provides portable solutions for administering an ergoline derivative treatment. This portability may be especially critical for patients who are not in close proximity to a hospital or other treatment facility, such as those who live in remote areas or who may be traveling. Additionally, without being bound to any theory, there is believed to be a therapeutic benefit to administering a medicament that contains an ergoline derivative sooner than later after the onset of a migraine or other headache. Migraine and other headaches tend to advance in the degree of their severity over time, so the sooner the medicament can be delivered after an onset of headache symptoms, the greater the likelihood of reducing or mitigating the severity of the symptoms. In some situations, early recognition and treatment of migraine or other headache symptoms may allow for a lower effective dosage of an ergoline derivative than might otherwise be necessary with delayed treatment. Moreover, lower effective dosages can help to avoid or reduce side effects often associated with ergoline derivatives, thereby increasing user acceptance of ergoline derivative and generally improving user experience.

Various embodiments of the present invention will now be described in more detail.

I. Medicament

A. Ergoline Derivative

Various ergoline derivatives may provide an effective treatment for headaches. Naturally occurring ergoline derivatives include ergotamine and ergometrine. Ergotamine is an ergopeptine which may be used to treat headaches. Ergotamine may sometimes be provided in combination with caffeine. Synthetic derivatives include dihydroergotamine or DHE, methysergide, ergoline mesylates, bromocriptine, pergolide, and lisuride. Synthetic DHE and methysergide may be used to treat headaches. Dihydroergotamine is known chemically as ergotaman-3',6',18-trione, 9,10-dihydro-12'-hydroxy-2'-methyl-5'-(phenylmethyl)-, (5'α)-,monomethanesulfonate, and has the chemical formula: $C_{33}H_{37}N_5O_5$. Dihydroergotamine mesylate is a hydrogenated version of dihydroergotamine. Specifically, dihydroergotamine mesylate is hydrogenated in the 9, 10 position with a mesylate salt, providing ergotaman-3',6',18-trione,9,10-dihydro-12'-hydroxy-2'-methyl-5'-(phenylmethyl) (5'a)-, monomethanesulfonate with the chemical formula: $C_{33}H_{37}N_5O_5CH_4O_3S$. Dihydroergotamine mesylate is commercially available as DHE-45® and MIGRANAL®. The therapeutic activity of DHE in headaches is generally attributed to the agonist effect at 5-HT1D receptors. Two current theories have been proposed to explain the efficacy of 5-HT1D receptor agonists in headaches. One theory suggests that activation of 5-HT1D receptors located on intracranial blood vessels, including those on arteriovenous anastomoses, leads to vasoconstriction, which correlates with the relief of the headache. The alternative hypothesis suggests that activation of 5-HT1D receptors on sensory nerve endings of the trigeminal system results in the inhibition of pro-inflammatory neuropeptide release.

B. Solvent

The ergoline derivative may be dissolved in a solution of water or a physiologically compatible organic solvent, such as sterile isotonic saline, 1,3-butanediol, ethanol, 1,2-propylene glycol, polyglycols mixed with water, dimethyl sulfoxide, fatty alcohols, triglyercides, partial esters of glycerin, Ringer's solution, or the like. Medicaments may be prepared using methods that are standard in the art (see, e.g., Remington's Pharmaceutical Sciences, 16th ed., A. Oslo ed., Easton, Pa. (1980)). The ergoline derivative may be incorporated into the medicament either as a free base or as a pharmaceutically acceptable salt. Although the mesylate salt is generally preferred, any pharmaceutically acceptable salt of an ergoline derivative may be used, including, for example, the tartrate salt.

C. Other Agents and Excipients

An exemplary medicament may include a combination of different ergoline derivatives, other agents, and excipients. Various other agents and excipients may be selected to relieve pain, reduce gastric stasis, reduce nausea, and/or allow for a faster rate of drug absorption.

For example, the rate at which the medicament enters the bloodstream of a patient may be adjusted by including vasodilators or uptake enhancers (e.g., caffeine). In some embodiments, a medicament may include one or more ergoline derivatives combined with caffeine or another uptake enhancer. For example, a medicament may include ergotamine, DHE, and/or methysergide, combined with caffeine as an uptake enhancer. The caffeine may be added at between a 0.1:1 and 10:1 weight ratio relative to DHE, such as between a 0.5:1 and 5:1 weight ratio (e.g., a 1:1 weight ratio). Additional exemplary uptake enhancers include N-acetylcysteine, polyethylene glycols, cyclodextrin, glycerol, alkyl saccharides, lipids, lecithin, dimethylsulfoxide, and the like.

In some embodiments, a medicament may include an ergoline derivative combined with riboflavin (Vitamin B12), one or more triptans, and/or one or more analgesics to relieve or mitigate migraine symptoms. Exemplary triptans include sumatriptan, rizatriptan, and zolmitriptan. Exemplary analgesics include acetaminophen, non-steroidal anti-inflammatory drugs (NSAIDs), opioids, muscle relaxants, anxiolytics, immune selective anti-inflammatory derivatives (ImSAIDs), and local anesthetics. Exemplary NSAIDs include aspirin, celecoxib, diclofenac, diflunisal, etodolac, ibuprofen, indomethacin, ketoprofen, ketorolac, nabumetone, naproxen, oxaprozin, piroxicam, salasalate, sulindac, and tolmetin. Exemplary opioids include codeine, morphine, hydrocodone, and oxycodone. Exemplary muscle relaxants include carisoprodol, cyclobenzaprine, diazepam, orphenadrine, and trizanidine. Exemplary anxiolytics include barbiturates, benzodiazepines, carbamates, and sympatholytics. Exemplary local anesthetics include lidocaine, procaine, prilocaine, and tetracaine.

One or more antiemetics may be included to reduce nausea, a common side effect of ergoline derivatives and analgesics. Exemplary antiemetics include setrons, antidopaminergics, neurokinin antagonists, dimenhydrinate, metoclopramide, and meclizine.

An exemplary medicament may additionally include various additional ingredients, preservatives, pH maintaining and/or pH adjusting agents, tonicity agents, antioxidants and stabilizers, nonionic wetting or clarifying agents, viscosity modifiers, and the like. One or more preservatives may be included to protect against microbial proliferation. Suitable preservatives include polyquaternium-1, benzalkonium chloride, thimerosal, chlorobutanol, methyl paraben, propyl paraben, phenylethyl alcohol, disodium edetate, sorbic acid, benzethonium chloride, and the like. The preservative should be selected and employed at a level sufficient to be active against bacteria, molds, yeasts, and fungi at low inclusion levels, maintain activity through medicament preparation, shelf life and usage, while not compromising the quality or performance of the medicament and not adversely affect patient safety or tolerance of the product. Typically such preservatives are employed at a level of from 0.001% to 1.0% by weight.

A pH maintaining and/or pH adjusting agent, such as a buffer, may be included to protect the medicament from any sudden change in pH that may otherwise accelerate degradation of the components or inhibit the efficacy of the medicament. Suitable buffers include boric acid, methanesulfonic acids, sodium hydroxide, sodium and potassium bicarbonate, sodium and potassium borates, sodium and potassium carbonate, sodium acetate, sodium biphosphate and the like. In some embodiments, one or more buffers may be added in amounts sufficient to maintain the pH of the medicament at between about pH 3 to pH 8, such as between about pH 3 and 5 (e.g., between pH 3.4 and 4.9), or between about pH 6 and pH 8 (e.g. between about pH 7 and pH 7.5). In some embodiments, the pH of the medicament may be no less than about pH 6, including for example no less than about any of pH 6.5, 7, or 8 (such as about pH 7.5 or 8).

One or more tonicity agents may be included to render the medicament isotonic with body fluids. Pain and irritation may occur if the medicament is too hypertonic or too hypotonic. A tonicity agent adjusts the ability of the medicament to exert an osmotic force across a biologic membrane. For example, red blood cells, blood plasma and 0.9% sodium chloride solution contains approximately the same number of solute particles per unit volume and are termed iso-osmotic and isotonic. If a medicament does not contain the same number of dissolved species, i.e., if the medicament contains more (hypertonic) or less (hypotonic), then it may be necessary to alter the composition of the medicament to bring the tonicity into an acceptable range. Suitable tonicity agents include dextran 40, dextran 70, dextrose, glycerin, potassium chloride, propylene glycol, sodium chloride, and the like. Typically the medicament solution will have a sodium chloride equivalent in the range of 0.9 plus or minus 0.2%.

One or more antioxidants or stabilizers may be included in a medicament to inhibit or delay the oxidation of various components, either by specifically quenching free radicals or by chelation of redox metals in the medicament. Suitable antioxidants and stabilizers include sodium bisulfite, sodium metabisulfite, sodium thiosulfite, thiourea, caffeine, chromoglycate salts, cyclodextrins and the like. Suitable wetting and clarifying agents include polysorbate 80, polysorbate 20, poloxamer 282 and tyloxapol. Additionally, or in the alternative, a medicament may be sparged with a non-oxidizing gas, such as nitrogen and/or CO2 in order to prevent oxidative degradation.

One or more viscosity modifiers may be included to change the thickness or texture of the medicament. Exemplary viscosity modifiers include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like.

II. Delivery Device

An exemplary preassembled, prefilled, single-use delivery device is an autoinjector comprising a syringe containing the medicament, a hollow injection needle operably coupled to a distal end of the syringe; a dosing mechanism operably adjacent to a proximal end of the syringe; and a trigger mechanism that when actuated, causes the dosing mechanism to advance the syringe and the injection, and to discharge the medicament through the injection needle. Exemplary delivery devices may additionally include safety caps, locking mechanisms to prevent unintentional delivery, ergonomic handles, transparent chambers and syringes to confirm the syringe has not been used before, and trigger mechanisms that are easier for a user to operate when experiencing a headache.

A contemplated preassembled, prefilled single-use delivery devices in the present invention permit administration outside a clinical setting during a migraine attack with a dose accuracy of at least 90%. Other contemplated preassembled, prefilled, single-use delivery devices would be assembled using a vacuum stoppering process that sufficiently eliminates residual headspace and bubbles so that horizontal storage conditions will not affect stability of the formulation. Preferably the preassembled prefilled single-use delivery device would allow for self-administration and more preferably the preassembled, prefilled, single-use device would not require intervention by the user In some embodiments, the delivery device is not user adjustable with respect to dosage or dosing rate, thereby preventing inadvertent or intentional misuse of the delivery device and/or medicament by a user suffering from a migraine. More preferably the preassembled, prefilled, single-use delivery device would be an auto injector. In another embodiment, the preassembled, prefilled, single-use delivery device would further comprise a transparent chamber, which may be shaded to limit exposure to light, that permits the user to inspect the medicament before administration to verify the medicament is clear, colorless and free of particulates. In another embodiment, the preassembled, prefilled, single-use delivery device comprises a safety cap that protects the syringe and needle from damage, contamination, and shields the user from inadvertent exposure to the needle.

A contemplated syringe would comprise a 25-30 gauge needle where the needle has a length sufficient for subcutaneous injection. Ina preferred embodiment, after administration of the medicament, the needle would recess into the delivery device to prevent repeated injections.

The present disclosure is also directed to methods using predominately gross motor movements of the user to self-administer an ergoline derivative medicament while experiencing a headache. Moreover, the present disclosure is directed to systems or kits that contain one or more delivery devices, and user instructions for self-administering a medicament that includes an effective low concentration dose of an ergoline derivative. The user instructions may include a mnemonic device to help remind a user how to administer the medicament and to help comfort a user who may be experiencing a headache when attempting to administer the medicament.

Although various persons, including, but not limited to, a patient or a healthcare professional, can operate or use exemplary embodiments of the present invention, for brevity an operator, patient or user will be sometimes referred to generally as a "user".

The term proximal refers to the direction pointing towards an injection site on a user's own body, and the term distal refers to the direction pointing away from the injection site.

Referring now to the drawings, exemplary delivery devices and systems will be described in further detail. FIG. 1 shows a perspective view of an exemplary delivery device 100 according to the present disclosure. The delivery device 100 includes a housing that defines a handle 102 and a cartridge 104. The handle 102 provides a location for a user to grip the delivery device. The handle also houses a dosing mechanism 150, which is discussed in more detail below with reference to FIGS. 3A and 3B. The cartridge contains or houses a syringe 106 which has been pre-filled with a medicament. A hollow injection needle 108 is operably coupled to a distal end of the syringe. The cartridge additionally houses the injection needle. A safety cap 110 attaches to the cartridge 104 to keep the injection needle sterile, protect the user from inadvertently contacting the injection needle, and to protect the needle from damage and contamination. A trigger mechanism such as a trigger button 112 actuates the dosing mechanism inside the handle 102 as discussed below. As shown in FIG. 1, the trigger button 112 is located at a distal portion of the handle 102, but one or more trigger buttons also may be located elsewhere on a delivery device 100 accordance with the present disclosure.

In the illustrated embodiment, the delivery device 100 is pre-assembled and comprises a single-use auto-injector. The pre-filled syringe 106 is installed in the cartridge 104. The cartridge 104 is then connected to the handle 102. In one embodiment, the connection between the cartridge 104 and handle 102 is via interlocks to prevent disassembly and/or tampering with the syringe 106 or dosing mechanism.

To initiate an auto-injection, a user removes the safety cap 110 from the delivery device 100, presses the proximal end of the cartridge 104 against an injection site such as a thigh or other suitable injection site, and then squeezes or presses the trigger button 112. The trigger button actuates the dosing mechanism, causing the syringe 106 (and sterile injection needle) to advance out of the proximal end of the cartridge 104. The advancing syringe causes the injection needle 108 to puncture the injection site and penetrate to an appropriate depth, such as 6-10 mm for subcutaneous delivery while avoiding muscle. The dosing medication continues to advance, ejecting a dose of the medicament housed in the syringe out of the injection needle. In some embodiments, a delivery device may include a window 114. In additional embodiments, the cartridge 104 is clear. Before use, the window 114 or clear cartridge 104 allows the user to view at least a portion of the syringe and/or at least a portion of the injection needle, such as to confirm that the solution is not contaminated (e.g., clear or colorless, and not cloudy or containing particles), or to confirm that an unused syringe is housed in the cartridge. During use, the window 114 or clear cartridge 104 allows a user to confirm that the medicament has been fully ejected from the syringe 106 before removing the delivery device 100 from the injection site.

A user may be experiencing an intractable headache such as a migraine headache when attempting to self-administer a medicament dose. The presently disclosed delivery devices include features configured to make the delivery device easier for a user to operate when experiencing a headache. These features include aspects of the safety cap, the handle, and the trigger mechanism, as described in more detail below.

Still referring to FIG. 1, the safety cap 110 of the delivery device 100 includes a flare 118 configured to facilitate removal of the safety cap with minimal reliance on fine motor skills. The flare 118 may be straight or curvilinear 116 as illustrated. The narrow portion of the flare 118 and/or curvilinear surface 116 may fit comfortably into the thenar space of a user's hand, allowing the user to pull the safety cap away from the cartridge using a gross arm movement. The safety cap 110 may thereby be removed even with a partial thenar grasp on the safety cap, and without requiring fine motor movements such as thumb and forefinger grasping. The wider portion of the flare 118 may provide an improved grip, preventing the safety cap from slipping from the user's thenar space when pulling, such as with a partial grasp on the safety cap.

The configuration of the safety cap 110, including the flare 118 and/or curvilinear surface 116 also may allow a user to grip the safety cap with something other than the thenar space of the user's hand, thereby expanding the possible ways to remove the safety cap. For example, the flare 118 and/or curvilinear surface may facilitate gripping the safety cap in a user's armpit (axilla), elbow pit (cubital fossa), or knee pit (popliteal fossa). Additionally, a user may wedge the safety cap between a user's leg (e.g., a posterior thigh) and a surface of a seat where the user is sitting, thereby relying on the weight of the user's leg to grip the safety cap while the user pulls on the handle 102. When removing the safety cap 110 in this manner, the delivery device tends to remain in close proximity with the user's anterior thigh, which is a typical injection site. As such, the amount of gross movement required to self-administer a dose of the medicament can be minimized, which may increase ease of use and improve comfort to a user who is experiencing a headache.

Referring again to the trigger button 112, as shown, the trigger button includes a broad surface 122, which facilitates squeezing or pressing the trigger button using any of a variety of different motor movements. The broad surface 122 of the trigger button facilitates reliance predominately on gross motor movements to press or squeeze the trigger button. For example, the broad surface of the trigger button may be actuated by the palm or heel of the user's hand, the user's forearm or elbow, or the user's torso, as necessary or convenient.

Figure 2:
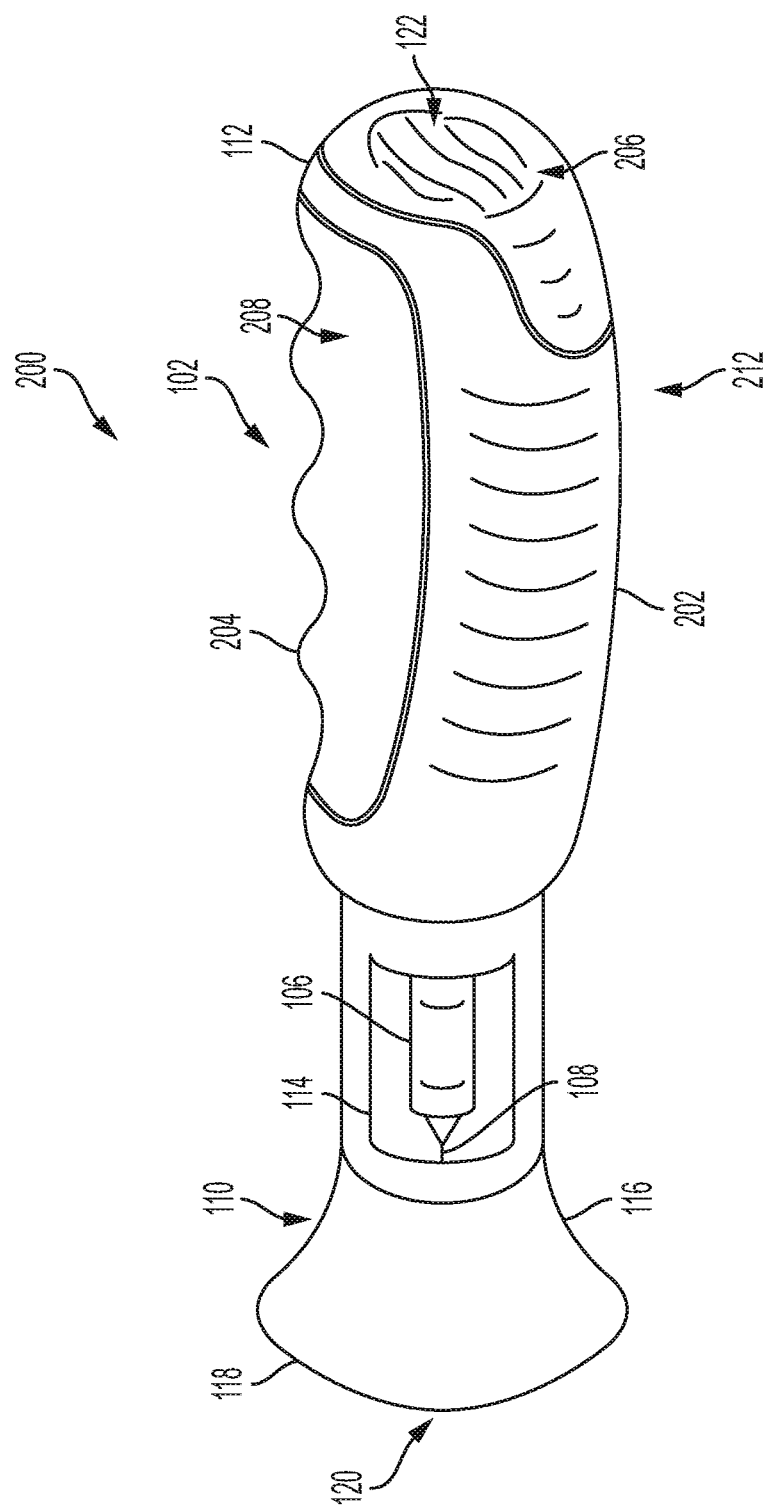
FIG. 2 is a perspective view of another exemplary delivery device according to the present disclosure.

Now turning to FIG. 2 a delivery device 200 according to another example may include an ergonomic handle 212. The ergonomic handle may include a plurality of curvilinear surfaces configured to ergonomically fit the contours of a user's hand. For example, these curvilinear surfaces may include a convex palm contour 202, a plurality of finger ridges 204, and a thumb depression 206. The thumb depression 206 may be part of the trigger button 112, for example, providing a broad surface 122 with a depression configured to receive a user's thumb. In some embodiments, the handle 212 (whether an ergonomic handle or otherwise) may include an additional or alternative trigger mechanism, such as a squeezable handle trigger 208, to actuate the dosing mechanism. The squeezable handle trigger 208 may be provided in addition or as an alternative to the trigger button 112. When the delivery device 200 includes both a trigger button 112 and a squeezable handle trigger 208, these trigger mechanisms may be configured to provide the user with the option to actuate the dosing mechanism using the trigger button 112, the squeezable handle trigger 208, or both. Thus, in some embodiments, the squeezable handle trigger and the trigger button may both actuate the dosing mechanism whether triggered individually or in combination, sequentially or simultaneously. These options allow the user to choose both the trigger mechanism as well as an approach for operating the chosen trigger mechanism that may feel comfortable. Such improvements in user-comfort when self-administering the medicament may, in turn, improve the reliability of the user in causing the trigger mechanism to successfully actuate the dosing mechanism.

Still referring to FIG. 2, the delivery device 200 includes a safety cap 110 having a curvilinear surface 116 with a flare 118 configured to facilitate removal of the safety cap with minimal reliance on fine motor skills as described above with respect to FIG. 1.

In some embodiments, the safety cap 110 may include a suction cup 120 located at a proximal portion of the safety cap. The suction cup may be configured to provide a partial vacuum with sufficient holding force to allow the user to pull the safety cap 110 off of the delivery device 200 when the suction cup 120 is attached to a suitable surface such as a table top, a wall, a window, or the like. The suction cup 120 facilitates removal of the safety cap 110 using a two-step gross motor movement. A user may perform all or part of this two-step gross motor movement using their arm or arms which the delivery device is grasped, or their torso, or combinations thereof. For example, the user may first plunge the suction cup onto a suitable surface with a gross motion of the user's arm(s) or torso. Then, the user may remove the safety cap by pulling on the delivery device handle 102 in a direction opposite the surface to which the suction cup has been secured, again with a gross motion of the arm(s) or torso. As discussed below, the inclusion of a suction cup 120 on the proximal end of the safety cap expands the number of possible ways that the safety cap can be removed from the delivery device, as well as the range of possible gross motor movements that can be utilized when removing the safety cap. These possibilities give options to the user, which allow the user to choose an approach that may feel most convenient or comfortable when self-administering the medicament.

Figure 3A:
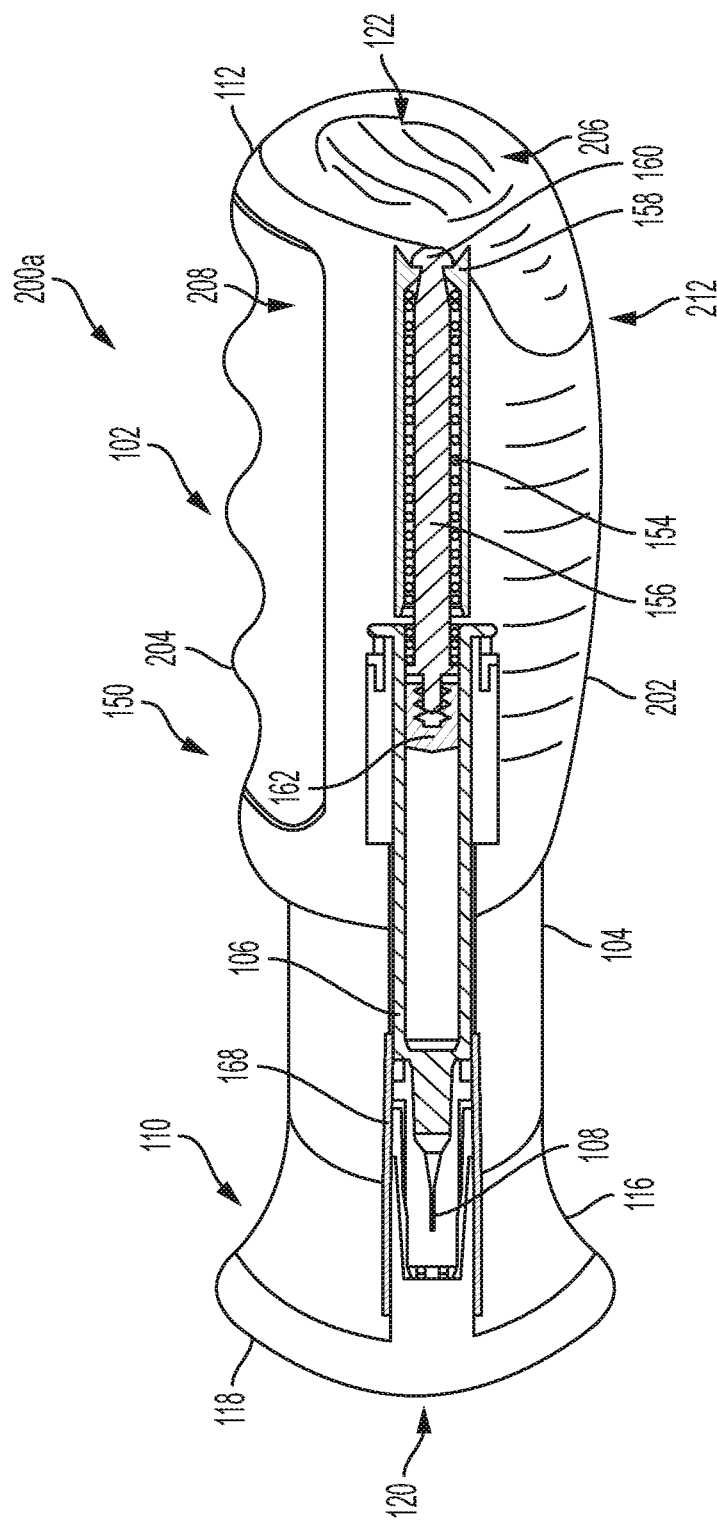
FIG. 3A is a partial cutaway view of delivery device of FIG. 2 with a first dosing mechanism.

A dosing mechanism 150 according to a first example is shown in FIG. 3A, which provides a partial cutaway view of the delivery device 200 of FIG. 2. Dosing mechanism 150 may also be used in delivery device 100 of FIG. 1. As shown in FIG. 3, an exemplary delivery device 200a includes a cartridge 104 operably coupled to a dosing mechanism 150. The cartridge 104 includes an inner cartridge sleeve 152, which may be provided either as an integral part of a cartridge 104 or as a separate component fitted within the cartridge 104.

Within the handle 102, a piston rod 154 is provided for ejecting a dose of medicament from the syringe 106. The piston rod 154 is held in a ready-to-dose or "armed" position under pressure of an injection spring 156 by a pawl member 158 releasably interfacing with a retaining member 160. The proximal end of the spring is secured to the piston rod at about the position where the piston rod interfaces with a plunger 162 of the syringe 106. The rate of the dosing mechanism depends on the spring rate and degree of compression applied to the injection spring 156. In one example, the degree of compression of the injection spring 156 is predetermined and not user adjustable so as to provide a predetermined desired dosing rate. This prevents against misadjustment or other inadvertent misuse of the delivery device 200.

Further referring to FIG. 3A, the cartridge 104 contains a syringe 106 that has been pre-filled with a medicament 320. The syringe 106 is coupled to a hollow injection needle 108. A safety cap 110 protects the syringe 106 and needle from damage and contamination, and shields the user from inadvertent exposure to the needle. In some embodiments, the safety cap 110 may additionally include a needle shield. The needle shield may further improve safety and protect the needle from damage and contamination. The needle shield may be formed as an integral part of the safety cap or a separate component coupled to the safety cap, such that the needle shield is withdrawn when the safety cap is removed.

The plunger 162 seals the medicament within the syringe 106. The piston rod 154 may extend partially into the syringe 106, abutting the plunger 162. A movable safety shield 168 may be provided.

After the safety cap 110 is removed, the delivery device 100 may be placed on an injection site, pushing safety shield 168 inward. When the piston rod 154 is released from retaining member 160, the spring 156 pushes the syringe away from the handle 102 and toward the injection site. When the syringe 104 reaches the end of its travel within the cartridge 104, the injection spring 156 further pushes the piston rod 154 into the syringe, depressing the plunger 162, delivering the medicament though the needle 108. After use, when the delivery device 100 is removed from the injection site, the safety shield 168 may return to its protective position to enclose the needle 108 and protect against inadvertent contact with the needle 108.

Figure 3B:
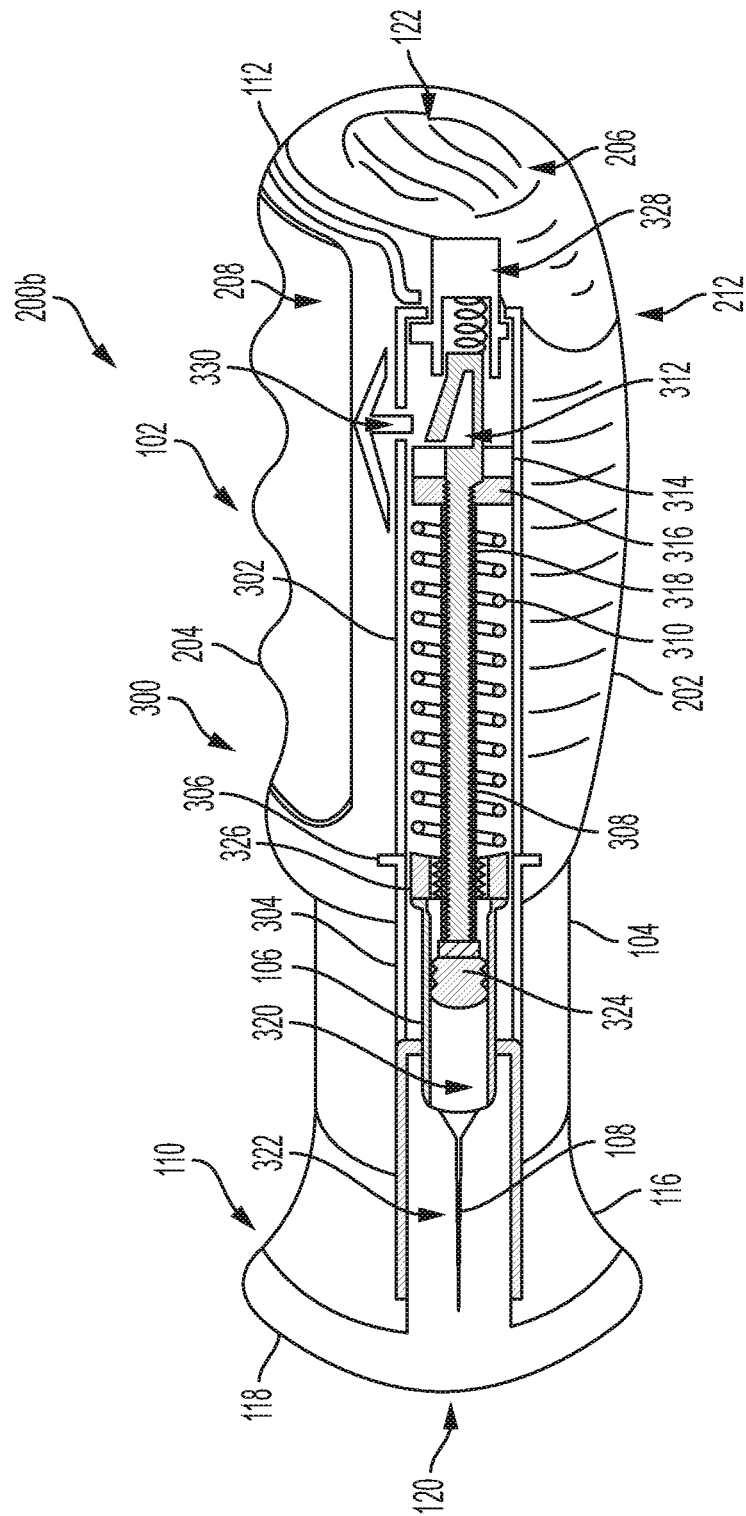
FIG. 3B is a partial cutaway view of the delivery device of FIG. 2 with a second dosing mechanism.

A dosing mechanism 300 according to a second example is shown in FIG. 3B, which provides a partial cutaway view of the delivery device 200 of FIG. 2. Dosing mechanism 300 may also be used in delivery device 100 of FIG. 1. As shown in FIG. 3B, an exemplary delivery device 200b includes a cartridge 104 operably coupled to a dosing mechanism 300. The dosing mechanism 300 includes a handle sleeve 302, which may be provided either as an integral part of the handle 102 or as a separate component fitted within the handle. The cartridge includes a cartridge sleeve 304, which similarly may be provided either as an integral part of a cartridge or as a separate component fitted within the cartridge. The cartridge and/or the cartridge sleeve may be operably coupled to the handle and/or the handle sleeve by a coupling 306 providing a snap-fit or other coupling interface. This coupling may be a removably couplable, for example, to facilitate reloading the delivery device with a fresh cartridge or syringe, or for switching between different cartridges or different handles. The delivery device may be reloaded by removing and discarding a spent cartridge and replacing the discarded cartridge with a fresh cartridge containing an unused syringe. Alternatively, the spent cartridge may be refilled with an unused syringe, with or without removing the spent cartridge from the handle of the delivery device. Alternatively, the delivery device may be regarded as a disposable product, to be discarded after a single-use.

Within the handle sleeve 302, a piston rod 308 is provided for ejecting a dose of medicament from the syringe 106. The piston rod 308 is held in a ready-to-dose or "armed" position under tension of a tension spring 310 by a pawl member 312 releasably interfacing with a retaining member 314. The proximal end of the tension spring 310 is secured to the handle sleeve at about the position where the cartridge 104 adjoins the handle 102. The distal end of the tension spring is secured to a nut member 316 that interfaces with helical threads 318 on the piston rod. When the piston rod 308 is released from the armed position, the pawl member 312 at the distal end of the piston rod slides through a passage way in the retaining member 314 under tension from the tension spring 310. As the pawl member slides through the passage way, the tension spring 310 advances the piston rod 308 and the nut member 316 in the proximal direction, with the proximal end of the piston rod extending into the syringe. The rate of the dosing mechanism depends on the degree of tension applied to the tension spring 310. The tension spring may be selected to have a predetermined amount of tension so as to provide a desired dosing rate. Additionally, or in the alternative, a preload may be applied in a specified amount, using a tension adjuster or dial. Nut guides or tracks (not shown) inside a distal portion of the handle sleeve 302 prevent the nut from rotating. As the piston rod continues to advance, the nut member moves free of the nut guides or tracks, which allows pre-loaded torsion in the tension spring to retract the piston rod, as will be discussed below.

Further referring to FIG. 3B, the cartridge 104 contains a syringe 106 that has been pre-filled with a medicament 320. The syringe is coupled to a hollow injection needle 108. A safety cap 110 protects the syringe and needle from damage and contamination, and shields the user from inadvertent exposure to the needle. In some embodiments, the safety cap 110 may additionally include a needle shield 322. The needle shield 322 may further improve safety and protect the needle from damage and contamination. The needle shield may be formed of an elastomeric material such as natural or synthetic rubber, open or closed cell foam or the like, within which the needle 108 is embedded. The needle shield may be formed as an integral part of the safety cap or a separate component coupled to the safety cap, such that the needle shield is withdrawn when the safety cap is removed. A plunger 324 seals the medicament within the syringe 106. The piston rod 308 may extend partially into the syringe 106, abutting the plunger 324.

The piston rod 308 is coupled to the syringe 106 by a one-way coupling 326. The syringe 106 and the one-way coupling 326 may be coupled together by a snap-fit connection or other suitable means, or the syringe and one-way coupling may be held adjacent to one another and in an operable position by a syringe coupling (not shown) and/or by grooves or guiding tracks in the cartridge sleeve 304 (not shown). The one-way coupling 326 includes an array of angled teeth which interface with a corresponding array of angled teeth on the piston rod 308. The interface between these angled teeth allow the piston rod 308 to move towards the proximal end of the cartridge and into the syringe 106, thereby depressing the plunger 324 and expelling a dose of the medicament from the syringe. Conversely, when the piston rod is retracted, the angled teeth resist the retracting force of the piston rod, thereby retracting the syringe and injection needle distally into the cartridge sleeve.

To trigger the delivery device 200, a user presses or squeezes the trigger mechanism (i.e., the trigger button 112 and/or the squeezable handle trigger 208). The trigger mechanism may include a spring-loaded actuating lever 328 that operably interfaces with the trigger button 112. When the trigger button is actuated, the spring-loaded actuating lever 328 advances over the pawl member 312 through the course of a trigger stroke, with the pawl member passing into a chamber within the actuating lever 328. The circumference or cross-sectional diameter of the chamber within the actuating lever is narrower than the cross-sectional width of the pawl member. As such, the walls of the actuating lever chamber compress the pawl member as the actuating lever advances in the proximal direction over the course of a trigger stroke, until the cross-sectional width of the pawl member becomes small enough to fit through the passage way in the retaining member 314. With the pawl member 312 thereby freed from the retaining member 314, the piston rod 308 becomes free to advance in the proximal direction under tension from the tension spring 310.

The trigger mechanism additionally or alternatively may include a spring-loaded actuating pin 330 that operably interfaces with the squeezable hand trigger 208. When the squeezable handle trigger 208 is actuated, the spring-loaded actuating pin 330 advances against the pawl member 312 over the course of a trigger stroke, thereby compressing the pawl member to a cross-sectional width capable of passing through the passage way in the retaining member 314.

The actuating lever 328 and the actuating pin 330 are configured and arranged to cooperate with one another such that one or both of them may be used individually or in combination, sequentially or simultaneously, to compress the pawl member without interfering with one another. This gives users the option of triggering the delivery device 100 using predominately or exclusively the trigger button 112, using predominately or exclusively the squeezable handle trigger 208, and/or using both the trigger button and the squeezable handle trigger in various proportions and in constant or varying degrees for all or part of the trigger stroke. As such, the motion and force required for triggering the delivery device may be shared by the trigger button and the squeezable handle trigger, thereby availing the user of multiple possible techniques for triggering the delivery device. These multiple possible techniques allow the user to choose a technique that may feel comfortable or convenient when self-administering a dose of the medicament using the exemplary delivery device.

Additionally, this cooperation between the trigger button and squeezable handle trigger may reduce the possibility of a mis-trigger caused by a partially actuated trigger mechanism, a partially-compressed pawl member, or the like. For example, a user intending to press the trigger button 112 with a thumb might not fully compress the pawl member, due to inhibited fine motor skills or other reasons. However, by also squeezing the squeezable hand lever 208, the actuating pin 330 may assist the actuating lever 328 or take-over the trigger stroke as needed. Similarly, a user may struggle to fully compress the squeezable hand lever 208, but may nevertheless actuate the delivery device by leaning into the trigger button 112 with the torso or by some other technique.

Figure 4A:
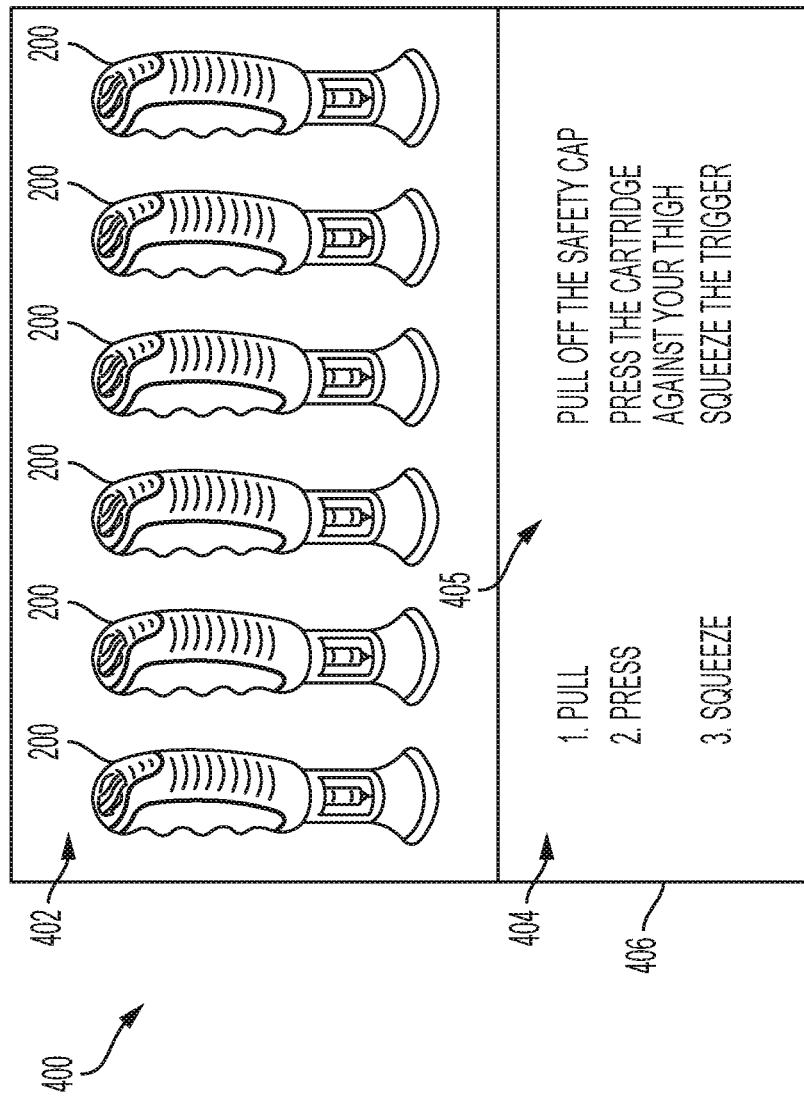
Figure 4B:
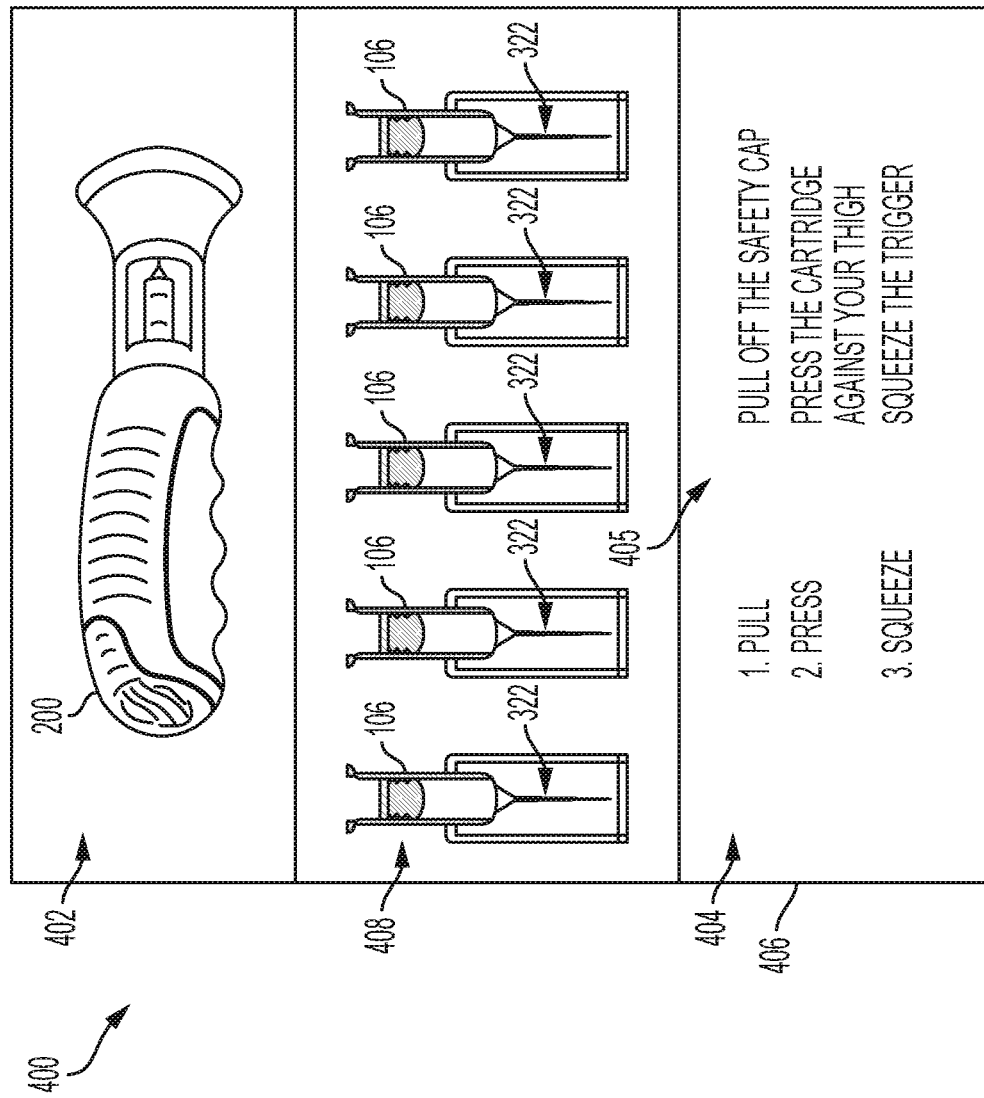

Now turning to FIGS. 4A-4C, the present disclosure further embraces systems or kits for administering a medicament. These kits may be used by a user to self-administer a medicament, or to administer the medicament for another person, without the need for a medical professional. As shown in FIGS. 4A-4C, a system or kit 400 for administering a medicament may include one or more delivery device 402, and user instructions 404 describing a method for administering a dose of the medicament. The user instructions may include a mnemonic device 405 to help remind the user how to administer the medicament. The mnemonic device 405 also may help comfort a user, who may be experiencing a headache when attempting to administer the medicament. For example, the mnemonic device may include the sequence: Pull, Press, Squeeze, as shown in FIGS. 4A-4C.

The system or kit may be provided in a carrying case or container 404, which may be configured various storage compartments such as foam cutouts to protect the delivery device or components thereof during transport, while providing a user with easy access to the system or kit at home or when traveling. In some embodiments, the carrying case or container may be waterproof, or may include other durability, ruggedness or robustness features. In some embodiments, a plurality of disposable or reusable delivery device may be provided. The delivery device may be pre-loaded with a syringe 106 containing a specified medicament dose, or various syringes may be provided separately to be loaded into the cartridge as needed.

For example, as shown in FIGS. 4B and 4C, a system or kit 400 may include a single reusable delivery device 402 and a plurality of cartridges or syringes 408. Such a reusable delivery device may be provided without a cartridge, or with an empty cartridge, in which case the device may be charged with a cartridge and/or a syringe from the system or kit. Alternatively, the single reusable delivery device may come with a first pre-filled syringe already loaded in the cartridge. The single delivery device may be refilled with a fresh cartridge or syringe after each use. In the embodiment shown in FIG. 4B, syringes are provided with a needle shield 322. The needle shield may be configured to interface with a reusable safety cap 110, such that after having been inserted into the cartridge, the needle shield will be withdrawn from the cartridge sleeve when the safety cap is removed. In another embodiment shown in FIG. 4C, the syringes are provided with a safety cap 110 already in place.

The present disclosure additionally embraces methods for administering a medicament using an delivery device. The medicament may be an ergoline derivative such as ergotamine or its synthetic form DHE or any other ergoline derivative. Some of the methods disclosed herein are tailored to help a user self-administer a medicament using an delivery device while experiencing a headache. As these acute symptoms may inhibit the user's fine motor skills, the presently disclosed methods include steps configured to accommodate any such inhibited fine motor skills.

An exemplary method of administering a medicament using an delivery device includes placing an delivery device against an injection site, actuating a trigger mechanism of the delivery device, and maintaining the delivery device against the injection site, while an injection needle penetrates the injection site, and a medicament contained in a syringe is injected though the injection needle into the injection site. In the exemplary method, the trigger mechanism, when actuated, causes a dosing mechanism of the delivery device to advance the syringe and the injection needle, and to discharge the medicament though the injection needle. The medicament may include 1.5 mg/mL or less of an ergoline derivative. The ergoline derivative may be dissolved in a solution of water or a physiologically compatible organic solvent.

Another exemplary method includes removing a safety cap from an delivery device, pressing a cartridge of the delivery device against an injection site on a user's own body, actuating a trigger mechanism of the delivery device, and auto-injecting a dose of the medicament into the injection site. The safety cap may be removed by any suitable means. For example, a user may grasp a curvilinear surface of the safety cap in the thenar space of the user's hand and pull the safety cap away from the cartridge using a gross arm movement. Alternatively, the user may wedge the safety cap between the user's posterior thigh and a seat where the user is sitting, and pull the safety cap away from the cartridge while relying on the weight of the user's leg to grip the safety cap.

In some embodiments, an delivery device may include a suction cup configured to facilitate removal of the safety cap. When using an delivery device with such a suction cup, the user may perform a two-step gross motor movement. The gross motor movement may include grasping the delivery device within one or both hands, and then plunging the suction cup into a suitable surface such as a table top, a wall, a window, or the like. The plunging motion may include a flexion and/or an extension of the user's arm(s) or wrist(s), and/or an abduction or adduction motion with respect to the user's torso. A typical plunging motion onto a flat surface such as a table top may include an extension of the elbow or wrist together with a rotation of the shoulder. Alternatively, a user may instead perform the plunging motion relying predominately on an adductive motion of the torso, bending towards the suitable surface such as a table, while grasping the delivery device in one or both hands and perhaps without much if any arm or wrist movement.

With the suction cup secured to a surface, an exemplary method continues with the user removing the safety cap by pulling on the delivery device handle 102 in a direction opposite the surface to which the suction cup is attached. This pulling motion may similarly be performed using gross motor movement of the user's arm(s), wrist(s), torso, or combinations thereof. For example, a typical pulling motion may include flexion of the elbow or wrist, together with rotation of the shoulder. Alternatively, a user may instead perform the pulling motion with an abductive motion of the torso, extending away from the table or other suitable surface while grasping the delivery device handle. In some embodiments the pulling motion may rely predominately on an abduction motion of the torso. The safety cap can be removed using the suction cup or otherwise, in any number of possible ways including a range of possible gross motor movements. These possibilities give options to the user, which allow the user to choose an approach that may feel comfortable or convenient when self-administering the medicament.

In an exemplary method, pressing or squeezing the trigger may include squeezing or pressing a trigger button and/or a squeezable handle trigger using any of a variety of different motor movements. A trigger button can be activated by grasping the handle 102 in one or both hands, in the way of a handle, and then squeezing or pressing the trigger button with one or both thumbs. Likewise, a squeezable handle trigger may be activated by grasping and squeezing with one or both hands, or any other similar technique. As alternatives, a trigger button or squeezable handle trigger may be pressed using the palm or heel of the hand, or the forearm or elbow. Moreover, a user may even activate the trigger button or squeezable handle trigger with an adductive motion of the torso. For example, a user may bend towards the trigger button, thereby wedging the delivery device between the user's torso and anterior thigh. As the user continues bending forwards, the user's adducting torso presses or squeezes the trigger button, thereby actuating the dosing mechanism. Similarly, a user may grasp a squeezable handle trigger with one or both hands, and then actuate the squeezable handle trigger predominately by the force exerted by the user's adducting torso. During these motions, the user may grasp the delivery device by with or without a hand, palm, thumb, or forefinger on the trigger button, and the broad surface 122 allows the trigger button to be pressed or squeezed predominately by gross motor movements.

In some embodiments, an delivery device 200 may include a squeezable handle trigger 208 configured to actuate the dosing mechanism. When the delivery device 200 includes both a trigger button 112 and a squeezable handle trigger 208, an exemplary method includes optionally actuating the dosing mechanism using the trigger button 112, the squeezable handle trigger 208, or both the trigger button and the squeezable handle trigger, sequentially or simultaneously. These options allow the user to choose an approach for actuating the dosing mechanism that may feel comfortable when the self-administering the medicament.

In some embodiments, an exemplary method includes a three-step gross motor movement to actuate a trigger button, a squeezable handle trigger, or both. This three-step gross motor movement may include a "lean-pull-lean" motion predominately involving torso movements while grasping the delivery device in one or both hands. This three step movement may be performed when seated in a chair facing a table or other suitable surface. For example, the method includes leaning towards a table or other suitable surface with a first gross motor leaning motion, thereby attaching a suction cup 120 on the proximal end of the cartridge to the surface with the first gross motor leaning motion. The method continues with pulling away from the surface with a first gross motor pulling motion, thereby removing the safety cap from the delivery device with the first gross motor pulling motion, and then subsequently leaning towards an injection site on a user's own body with a second gross motor leaning motion, such as a posterior thigh, thereby pressing the delivery device against the injection site with the second gross motor leaning motion. As this second gross motor leaning motion continues, the delivery device becomes wedged between the user's torso and posterior thigh, thereby pressing or squeezing the trigger mechanism, activating the dosing mechanism to inject a dose of the medicament into the injection site.

In some embodiments, pressing or squeezing a trigger mechanism may include pressing or squeezing one or both of the trigger button and the squeezable handle trigger, using predominately or exclusively the trigger button 112, using predominately or exclusively the squeezable handle trigger 208, and/or using both the trigger button and the squeezable handle trigger in various proportions and in constant or varying degrees for all or part of the trigger stroke. An exemplary method may include sharing a motion and force required for triggering a delivery device between a trigger button and a squeezable handle trigger. For example, pressing or squeezing the trigger mechanism may include pressing a trigger button through a first portion of a trigger stroke, and then completing the trigger stroke by squeezing a squeezable hand trigger; or pressing or squeezing the squeezable hand trigger through a first portion of a trigger stroke, and then completing the trigger stroke by pressing the trigger button.

The medicament may be injected at any suitable injection site, such as the posterior or anterior thigh, buttock, hip, abdomen, upper arm, or shoulder. Ergoline derivatives such as DHE may be injected intramuscularly or subcutaneously. Typically intramuscular injections provide for faster absorption, whereas subcutaneous injections may provide for further reduced side effects. Typical intramuscular injection sites include deltoid, dorsogluteal, rectus femoris, vastus lateralis and ventrogluteal muscles. Typical subcutaneous sites include fatty tissue of the abdomen, thigh, lower back, or upper arm. Thus, any suitable injection site may be selected. In some embodiments, user instructions 402 may include a description of recommended or alternative injection sites. Typically the injection needle 108 will be sized either for an intramuscular injection site, or a subcutaneous injection site.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A method of treating a headache in a person, comprising administering an ergoline derivative medicament using preassembled, prefilled, single use delivery device, the method comprising:
   placing the delivery device against an injection site;
   actuating a trigger mechanism of the delivery device, wherein the trigger mechanism, when actuated, causes a dosing mechanism of the delivery device to advance the syringe and the injection needle, and to discharge the medicament though the injection needle; and
   maintaining the delivery device against the injection site, while the injection needle penetrates the injection site, and the medicament contained in the syringe is injected though the injection needle into the injection site;
   wherein the medicament comprises a concentration range of about 0.3 mg/mL to about 1.5 mg/mL of an ergoline derivative.

2. The method of claim 1, wherein the dosing mechanism of the delivery device is not adjustable by the user.

3. The method of claim 1, wherein a dose amount delivered by the delivery device is not adjustable by the user.

4. The method of claim 1, wherein the ergoline derivative medicament comprises dihydroergotamine or a pharmaceutically acceptable salt thereof.

5. The method of claim 4, wherein the ergoline derivative medicament comprises dihydroergotamine and/or dihydroergotamine mesylate.

6. The method of claim 5, wherein the concentration of the ergoline derivative is about 1 mg/mL.

7. The method of claim 5, wherein a dose of the ergoline derivative ranges from about 0.5 mg to 3 mg.

8. The method of claim 5, wherein the delivery device is an autoinjector and the medicament is self-administered while the person is experiencing an onset of a headache.

9. The method of claim 8, wherein the headache comprises a migraine headache, a tension-type headache, or a cluster headache.

10. The method of claim 8, wherein the headache comprises hemicrania continua, new daily persistent headache, a post-traumatic headache, or a medication overuse headache.

11. The method of claim 8, wherein the injection needle has a length sufficient for subcutaneous injection, with a 25-30 gauge.

12. The method of claim 11, wherein the medicament is administered within 2 minutes or less after the onset of the headache.

13. The method of claim 11, wherein the medicament is administered within 5 minutes or less after the onset of the headache.

14. The method of claim 11, wherein the medicament is administered within 10 minutes or less after the onset of the headache.

15. The method of claim 11, wherein the medicament is administered within 20 minutes or less after the onset of the headache.

16. The method of claim 8, further comprising removing a safety cap from the auto-injector device.

17. The method of claim 16, further comprising removing the safety cap from the auto-injector device predominately using gross motor movements.

18. The method of claim 17, wherein removing the safety cap comprises gripping the safety cap with the thenar space of one hand and gripping the handle with another hand, and pulling the safety cap off of the cartridge, the safety cap comprising a flared cap with a narrow portion configured to fit comfortably into the thenar space of a user's hand.

19. The method of claim 17, wherein removing the safety cap comprises gripping the safety cap in an armpit (axilla), elbow pit (cubital fossa), or knee pit (popliteal fossa) and pulling on the handle with one or both hands, the safety cap comprising a flared portion configured to facilitate the gripping.

20. The method of claim 17, wherein removing the safety cap comprises wedging the safety cap between a posterior thigh of the user's leg and a surface of a seat and pulling on the handle with one or both hands, the weight of the user's leg gripping the safety cap while the person pulls on the handle, the safety cap comprising a flared portion to facilitate the wedging.

21. The method of claim 8, wherein the dosing mechanism comprises a piston rod retained in an armed position and keeping a spring under compression, the piston rod being in contact with a plunger of the syringe, and when the trigger is actuated, the piston rod is released from its retainer and the spring and piston rod urge the syringe in a direction toward the injection site.

22. The method of claim 21, wherein when the syringe reaches an end of its travel within the device, the spring and piston rod cause the plunger to travel through the syringe to dispense the medicament through the needle.

23. The method of claim 8, wherein the syringe is viewable inside the auto-injector, and the method further comprises visually checking the syringe prior to the step of actuating the trigger mechanism.

24. The method of claim 6, wherein the syringe is viewable inside the auto-injector, and the method further comprises visually checking the syringe while performing the step of maintaining the delivery device against the injection site.

25. An ergoline derivative containing medicament comprising dihydroergotamine or a pharmaceutically acceptable salt thereof, wherein the medicament is disposed in an auto-injector device, the device comprising:
a syringe containing the medicament;
a hollow injection needle operably coupled to a distal end of the syringe; a dosing mechanism operably adjacent to a proximal end of the syringe; and a trigger mechanism operably coupled to the dosing mechanism, wherein the trigger mechanism, when actuated, causes the dosing mechanism to advance the syringe and the injection needle, and to discharge the medicament though the injection needle; and
wherein the ergoline derivative is present in a concentration range of about 0.3 mg/mL to about 1.5 mg/mL.

26. The ergoline derivative containing medicament of claim 25, wherein the ergoline derivative is dihydroergotamine mesylate.

27. The ergoline derivative containing medicament of claim 25, wherein the concentration of the ergoline derivative is about 1 mg/mL.

28. The ergoline derivative containing medicament of claim 25, wherein the concentration of the ergoline derivative is about 1.5 mg/mL.

29. The ergoline derivative containing medicament of claim 25, wherein the concentration of the ergoline derivative is from about 0.5 to about 1.4 mg/mL.

30. The ergoline derivative containing medicament of claim 25, wherein the concentration of the ergoline derivative is from about 0.8 to about 1.2 mg/mL.

31. The ergoline derivative containing medicament of claim 25, wherein the auto-injector discharges a dose of between 0.5 mg to 3 mg of the ergoline derivative.

32. The ergoline derivative containing medicament of claim 25, wherein the medicament further comprises one or more tonicity adjusting agents, buffers, antioxidants, stabilizers, nonionic wetting or clarifying agents, and/or viscosity modifiers.

33. The ergoline derivative containing medicament of claim 25, wherein the medicament further comprises alcohol, glycerin, and water for injection.

34. The ergoline derivative containing medicament of claim 33, wherein the medicament further comprises a buffer and/or another pH adjusting agent.

35. The ergoline derivative containing medicament of claim 33, wherein the medicament further comprises sodium hydroxide or methane sulfonic acid.

36. The ergoline derivative containing medicament of claim 25, wherein the medicament comprises 1.0 mg dihydroergotamine mesylate, 49.0 mg ethanol, 150 mg glycerin, 800 mg water for injection, and a buffer comprising sodium hydroxide and/or methane sulfonic acid in an amount sufficient to attain the pH of the medicament to between 3.4 and 4.9.

* * * * *